United States Patent
Gallamore

[11] Patent Number: 6,149,615
[45] Date of Patent: Nov. 21, 2000

[54] OPTO-CUPPED PEDIA PATCH

[76] Inventor: Deborah Gallamore, 129 17th St., Washougal, Wash. 98671

[21] Appl. No.: 09/198,520

[22] Filed: Nov. 23, 1998

[51] Int. Cl.⁷ ........................................ A61F 13/12
[52] U.S. Cl. ................................ 602/61; 602/74
[58] Field of Search ........................ 602/74, 61

[56] References Cited

U.S. PATENT DOCUMENTS

| | | |
|---|---|---|
| 3,952,735 | 4/1976 | Wirtschafter et al. . |
| 5,769,806 | 6/1998 | Radow . |

*Primary Examiner*—Michael A. Brown
*Assistant Examiner*—Lalita M. Hamilton

[57] ABSTRACT

An improved occlusive self-adhesive eye patch, and a method of treatment for Amblyopia. A patch may successfully be applied over the left or right eye without restriction of eye movement or function. The patch comprises a non-adherent gauze pad or foam, having an adhesive for securing patch to the face over the eye socket. A slit from the patch's central bottom edge inward toward the center is present to allow for manual manipulation of the adhesive side transversely atop from the slit and adhering it to the non-adhesive side; therefore, the patch may be configured into an concavo-convex or outwardly cupped shape.

1 Claim, 2 Drawing Sheets

OPTO-CUPPED PEDIA PATCH

BACKGROUND OF THE INVENTION

The present invention relates to eye patches, and in particular these employed by Optometric personnel and/or for the treatment of Amblyopia (am-blee-oh-pee-ah), or lazy eye. An occlusive patch for covering the good eye of a patient suffering from Amblyopia to regain part of full visional function.

Lazy eye is the loss or lack of development of central vision in one eye that is unrelated to any eye health problem and is not correctable with lenses. It usually occurs before age six. Side vision is unaffected. Lazy eye usually results from failure to use both eyes together. It is often associated with crossed-eyes or a large difference in the degree of nearsightedness or farsightedness between the two eyes. Symptoms include noticeably favoring one eye or a tendency to bump into objects on one side. Symptoms, however are not always obvious.

The earlier lazy eye is diagnosed, the greater the chance for complete recovery. This is one reason why children should see an optometrist for a thorough eye examination by six months of age.

One of the obstacles to effective treatment of Amblyopia remains patient and parent non-compliance with the patching process, and this non-compliance may be a result from problems with patching. Personal experience has proven particularly how uncomfortable present occlusive patches are.

Various eye patches are disclosed in the prior art. For example U.S. Pat. No. 4,995,114; U.S. Pat. No. 5,769,806, as well as U.S. Pat. No. 5,389,066, applies various pressures to the eye as well as restricts eye movement. When a patient simply needs obscured vision for the treatment of Amblyopia such patching can be uncomfortable. Another example, U.S. Pat. No. 4,951,658, and U.S. Pat. No. 4,793,003 configures to conform flat against the eyelid forcing they eyelid to remain closed. For patients suffering from Amblyopia where it is not necessary to keep the eye closed whose eye may be patched for months at a time, this kind of patching and patch proves to be not only unnecessary but uncomfortable as well. Current patches can play a role in causing the patched eye to itch. This may be due to the lashes being pressed against the inner foam or pad thus smashing the eye lashes into the eyelid. Such discomfort ultimately makes it difficult in compliance with the needed patching as a treatment for Ambloypia for any extended period of time.

In the present invention a new improved occlusive eye patch. An eye patch that can be manipulated into a concavo-convex or outwardly cupped shape for the treatment of Amblyopia. Once patch is placed over the good eye of a patient suffering from Amblyopia, the present invention will allow the patient to benefit from having obscured vision while allowing the eye to carry out normal eye functions namely blinking without pressure to the eyelid and without restriction of normal eye movement.

Alternative means of patching may be used however they have proved to be unsuitable for children. Case in point, The Pirate Patch, a black reusable eye patch which has an elastic band which holds the patch in place. Such eye patching is ineffective as the child can move the patch to one side so that he can use his good eye to see around the patch.

SUMMARY OF INVENTION

In the object of the present invention to provide an improved eye patch. Another object of the present invention is to provide an improved eye patch for the treatment of Amblyopia. Yet in addition to provide an eye patch which can be manipulated into a concavo-convex or outwardly cupped shape; allowing the wearer to carry out normal eye functions, namely blinking without pressure or restrictions from the eye patch itself. A general object is to provide an eye patch which can adhere to the skin, over the eye socket with a concavo-convex self-adherent eye patch. Providing a patient suffering from Amblyopia with the greatest comfort from an occlusive eye patch while benefiting from obscured vision.

DETAIL DESCRIPTION OF THE INVENTION

Figure 1:
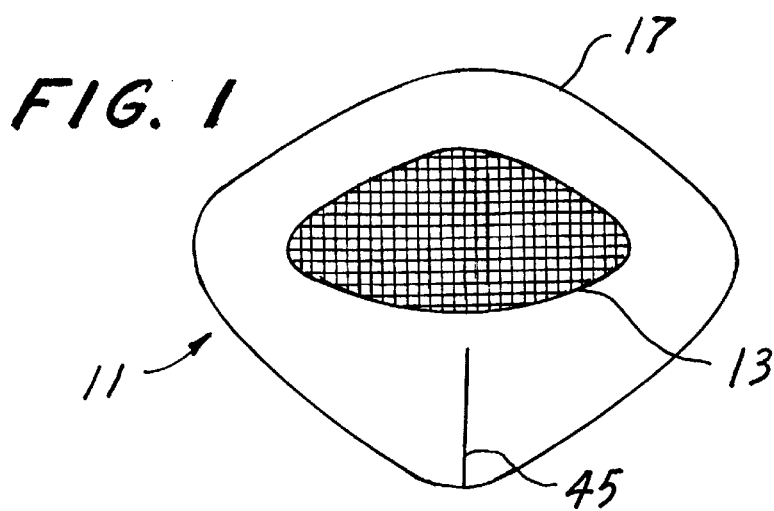
FIG. 1. is a top plan view of the eye patch of the invention.
Figure 2:
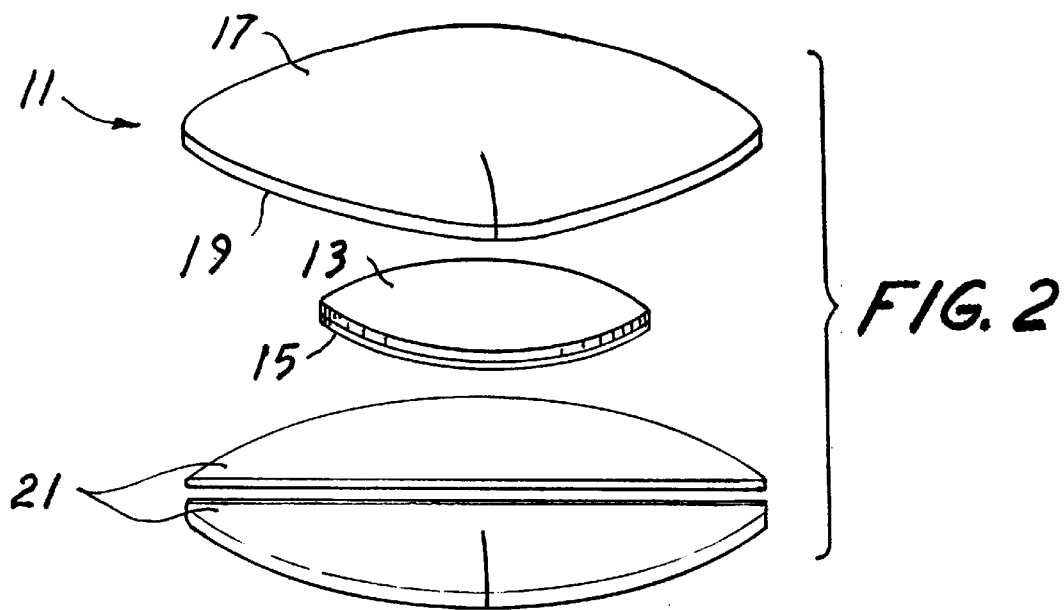
FIG. 2. is an exploded perspective view of the one embodiment of the eye patch.

Referring now to FIGS. 1 and 2, there is shown in eye patch 11 comprising an pad or foam 13 shaped to be manipulated into a concavo-convex shape having a nonadherent surface 15 on it's underside for placing near and not onto the eyelid. The upper surface of the pad or foam 13 is adhered to the outer membrane or cloth-like material by a layer of adhesive 19. Outer membrane or cloth-like material 17 and adhesive 19 on the underside thereof extend beyond the periphery of the pad or foam 13 in all directions exposing enough adhesive 19 to securely adhere the eye patch to the face over the eye socket. A removable protective liner 21 covers the nonadherent underside of the pad or foam 13 and the exposed adhesive 19 prior to use. A elongated slit 45 located at the patch's bottommost central edge, whereby a patient can manually manipulate patch into an concavo-convex or outwardly cupped shape through a slit 45 which extends all the way through the patch.

Figure 3:
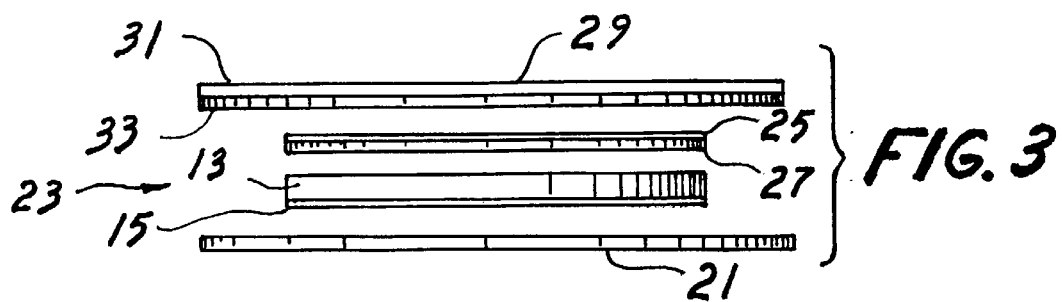
FIG. 3. is an exploded side elevational view of the second embodiment of the eye patch.

Referring now to the embodiment of FIG. 3. eye patch 23 comprises a pad or foam 13 an nonadherent surface 15 on it's underside for placing near and not on the eyelid, giving support to it's concavo-convex shape. The pad or foam and nonadherent surface are identical to those illustrated in FIG. 2. Eye patch 23 further comprised a outer membrane or cloth-like material 25 having a layer of adhesive 27 on it's under surface to adhere outer membrane or cloth-like material 25 to the top surface of pad or foam 13. Over the top surface of an outer membrane or cloth-like material 25 is adhered breathable tape 29 extends beyond the periphery on the pad or foam 13 and outer membrane or cloth-like material 25 in all directions to provide sufficient exposed adhesive 33 to securely adhere the eye patch to the face over the eye socket.

As in FIG.2. removable protective liners 21 covers the underside of the pad or foam 13 and the exposed adhesive 33 prior to use. The pad or foam 13 provides the needed support to eye patch to retain it's concavo-convex shape, and may comprise of any materials which can provide the inner support to prevent collapse of concavo-convex shape In the embodiment of FIG. 3., adhesive 27 which secures outer membrane or cloth-like material 25 to the pad or foam 13 may be different from the adhesive 33 which adheres to the patch to the skin.

Figure 4:
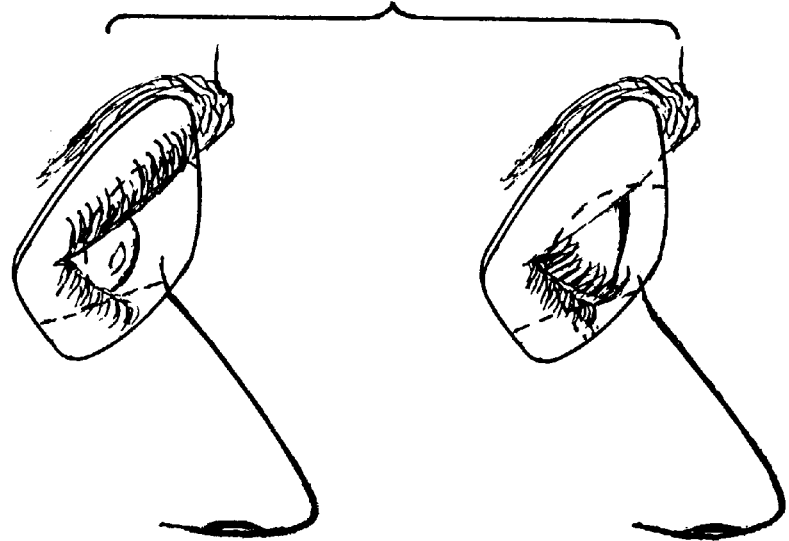
FIG. 4. is a side plan view of the eye patch after is has been adhered to the face, open eye & closed eye.

In the embodiment of FIG.4. occlusive patch 11 adhered to patients faces after it has been manipulated into a concavo-convex shape.

Figure 5:
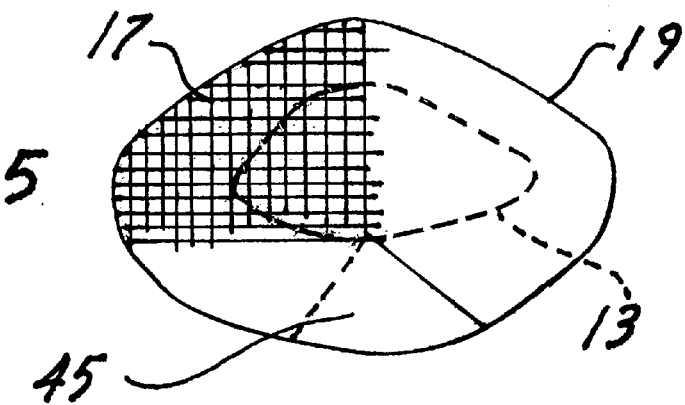
FIG. 5. is a top plan view after the adhesive side of the bottommost left part of the adhesive side and transversely adhering it atop the right non-adhesive side, configuring the eye patch into an concavo-convex or outwardly cupped shape.
Figure 6:
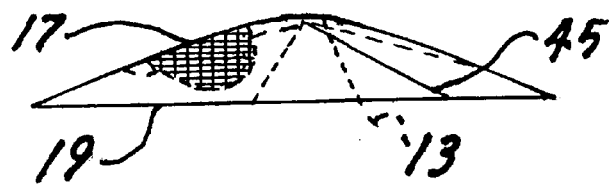
FIG. 6. is the side plan view after the bottommost left part of the adhesive side and transversely adhering it atop the right non-adhesive side, configuring the eye patch into an concavo-convex or outwardly cupped shape.

Referring to FIG.5 and 6. after where by the eye patch at the slit 45 has been manually manipulating from the bottommost left part of the adhesive side 19 and transversely adhering it atop the right non-adhesive side 17, configuring the eye patch into an concavo-convex or outwardly cupped shape.

REFERENCES CITED

| U.S. PATENT DOCUMENTS | | |
|---|---|---|
| 3,762,419 | 10/1973 | Walters |
| 3,908,645 | 09/1975 | Sandvig |
| 3,952,735 | 04/1976 | Wirtshafter et al. |
| 4,303,063 | 12/1981 | Stahl |
| 4,576,169 | 03/1986 | Williams |
| 4,599,746 | 07/1986 | Stoner |
| 4,727,869 | 03/1988 | Leonardi |
| 4,793,003 | 12/1988 | Riedel et al. |
| 4,951,658 | 08/1990 | Morgan et al. |
| 5,389,066 | 02/1995 | Rhame, Jr. |
| 5,431,622 | 07/1995 | Pyrozyk et al. |
| 5,769,806 | 06/1998 | Radow |

What I claim as my invention is:

1. A self-adherent occlusive eye patch comprising an outer membrane having an upper surface, a lower surface, and an outer edge, said outer membrane is superimposed over a pad, said outer membrane having a sit which extends vertically from the center of the edge of said membrane, whereby a patient can manually manipulate the patch into a concavo-convex outwardly shape.

* * * * *